Aug. 11, 1964 G. MILLER Plant Pat. 2,433
APPLE TREE
Filed Jan. 7, 1963 2 Sheets-Sheet 1
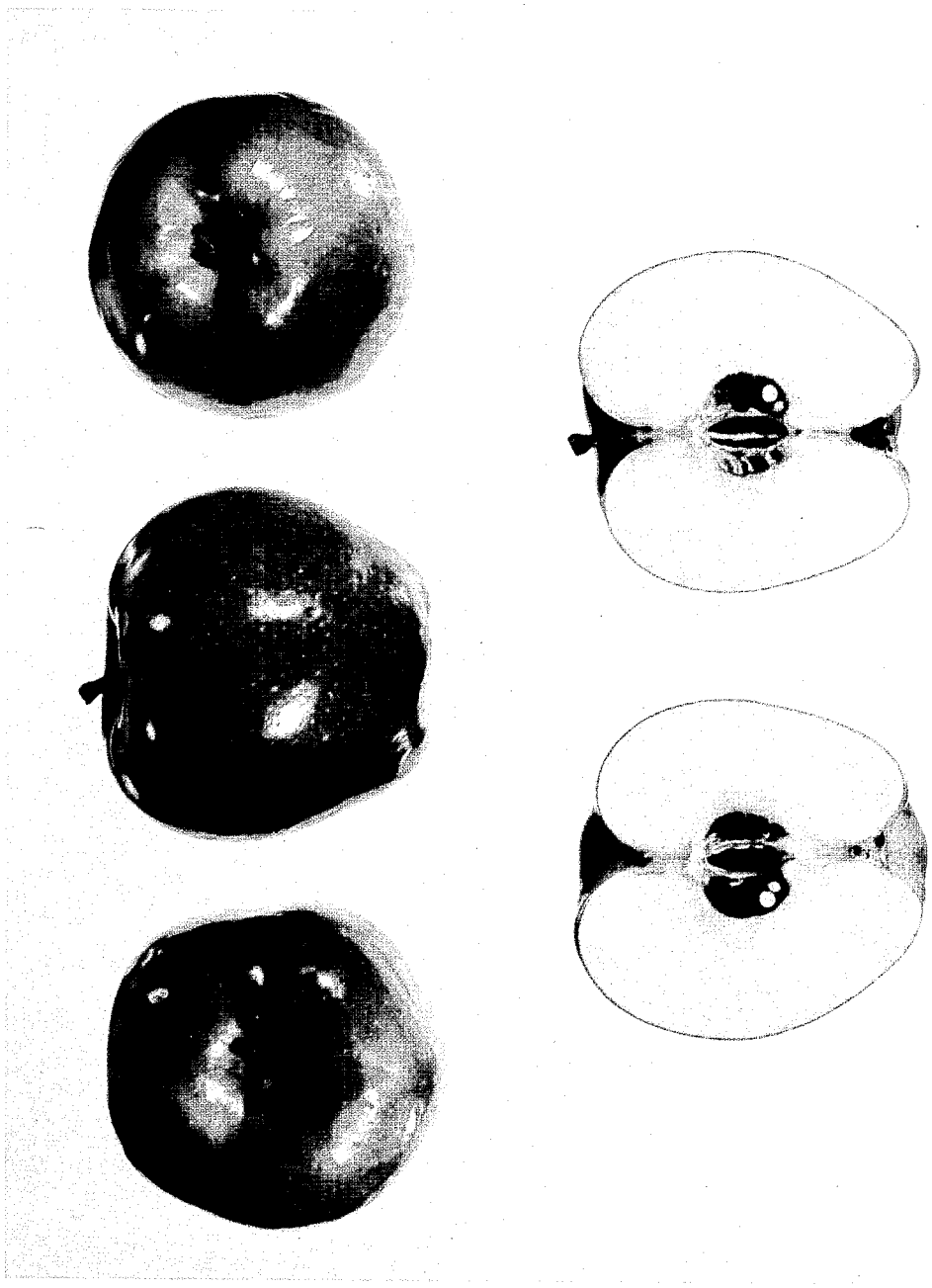
Inventor.
Gilbert Miller
By: Robb & Robb
Attorneys.

Aug. 11, 1964 G. MILLER Plant Pat. 2,433
APPLE TREE
Filed Jan. 7, 1963 2 Sheets-Sheet 2
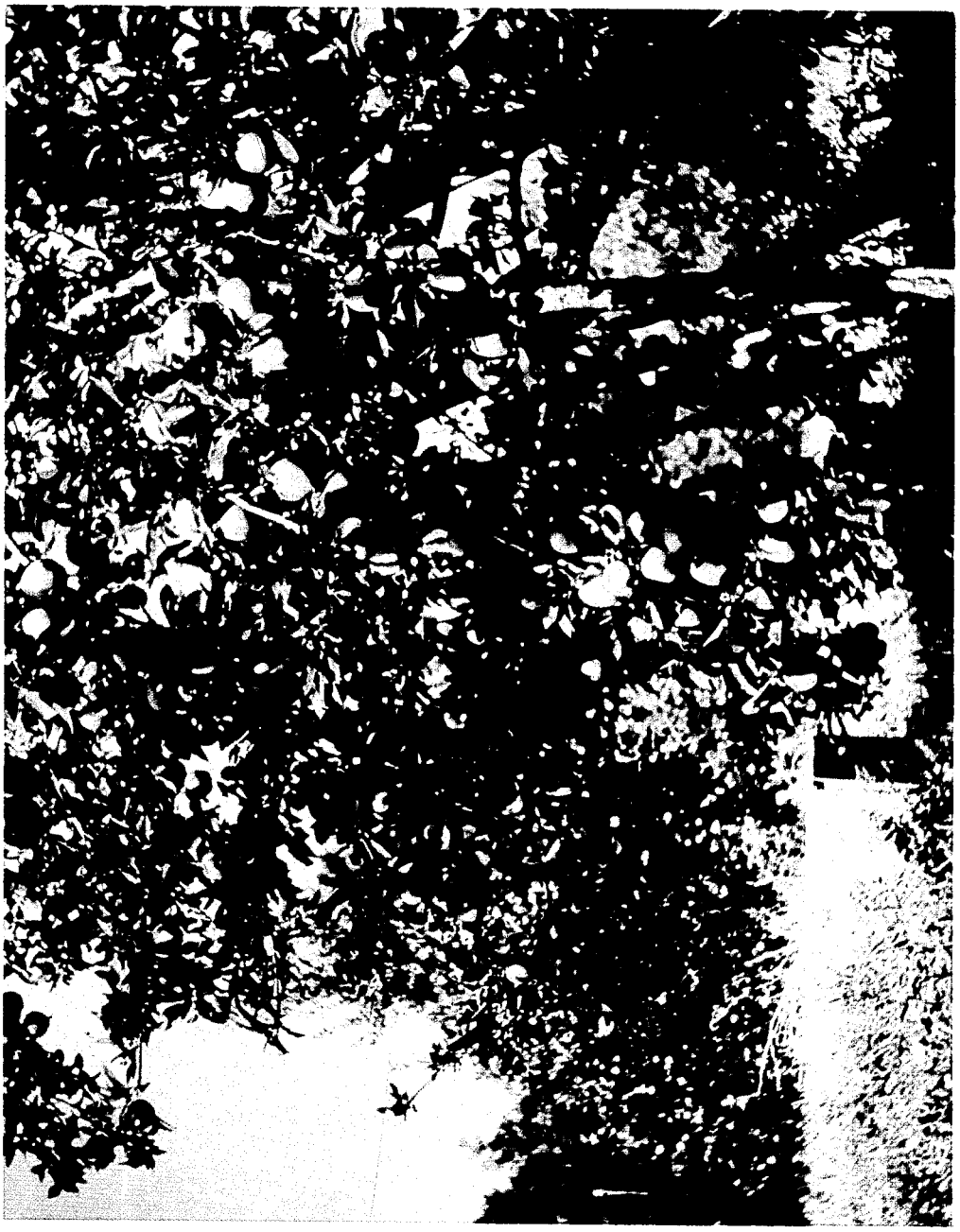
Inventor.
Gilbert Miller
By: Robb & Robb
Attorneys.

United States Patent Office

Plant Pat. 2,433
Patented Aug. 11, 1964

2,433
APPLE TREE

Gilbert Miller, Spring Gap, Md., assignor to Consolidated Orchard Company, Paw Paw, W. Va., a corporation of Virginia

Filed Jan. 7, 1963, Ser. No. 249,965
1 Claim. (Cl. Plt.—35)

The present invention relates to a new and distinct variety of apple tree which was discovered by me as a whole tree sport during the course of my supervision and care as production manager for the assignee of this application.

At the time of my initial discovery of the new variety aforesaid, I was supervising and directing the growing of apple trees of various varieties in one of the orchards of my assignee located near Cumberland, in Allegany County, in the State of Maryland. My attention was attracted to one particular tree in that orchard, amongst a block of apple trees known as the "Mood" strain of the "Delicious" variety, and normally sold under the trademark "Starking Delicious." The particular tree just referred to seemed to be characterized by striking, unusually Dark Green and large leaves which stood out in marked contrast to the leaves of other apple trees of various varieties being grown in this orchard, as well as by an unusually early coloring of the fruit, as compared with the normal coloring habits of all other varieties being grown in the same orchard and in the vicinity thereof. Further close inspection of the particular tree referred to in the foregoing, and continued observations thereof for several seasons, convinced me that it was a new and distinct variety, originated as a sport of unknown parentage, but probably a sport of the "Mood" strain of the "Delicious" referred to above, as evidenced by the following unique combination of characteristics which are outstanding in the new variety and which distinguish it from all other varieties of which I am aware:

(1) A true semi-dwarf habit of growth;

(2) Exceptionally large and lush Dark Green leaves, which are at least one or two shades darker than the foliage of all other so-called "Delicious" type apple varieties;

(3) A true spur-type, with early and heavy fruit-bearing habits;

(4) Relatively large fruit size;

(5) An early and uniform coloring habit of the fruit throughout the tree, regardless of lack of uniform exposure to sun, particularly with respect to the fruit borne towards the center and on other inner portions of the tree and when the fruit occurs on the same or adjacent limbs relatively close together, thereby eliminating the necessity of pruning the tree to thin out the limbs for better sun exposure as customarily required in the case of other spur-type apple varieties, such as the "Bisbee Apple" (Plant Patent No. 1,565), and the "Gilbert Apple" (Plant Patent No. 1,822), and thus assuring heavier fruit crops, all of which are highly important and advantageous features from a commercial standpoint;

(6) An attractive and distinctive full Dark Red fruit color which is free of striping and markings at maturity;

(7) An outstanding and true "Delicious" type fruit flavor; and (8) Good keeping and shipping qualities of the fruit.

Asexual reproduction of the new variety by both budding and grafting, as performed at Kearneysville, West Virginia, and elsewhere in the State of Maryland, shows that the foregoing characteristics and distinctions come true to form and are established and transmitted through succeeding propagations.

The accompanying drawings shown typical specimens of the foliage and fruit of my new variety, and the general habit of growth thereof, with certain of the fruit specimens being shown in cross-section, all as depicted in color as nearly true as it is reasonably possible to make the same in color illustrations of this character.

The following is a detailed description of the new variety, with color terminology in accordance with Nickerson's Color Fan, published by Munsell Color Company, Inc., of Baltimore, Maryland, except where general color terms of ordinary dictionary significance are obvious, said description being based upon observations made at Kearneysville, West Virginia, and in Allegany County, Maryland:

Dates of first and last pickings: About September 25 and about October 5, respectively.

Tree: Medium size; medium vigor; upright, low; vase-formed; slow growing; hardy; very productive; regular bearer.

*Trunk.*—Stocky; medium smoothness.

*Branches.*—Thick; medium smoothness; little-branched. Color—gray. Lenticels—few; small.

*Leaves.* — Large; thick; rugose; taper-pointed. Shape—ovate. Length—about 3¼ inches. Width—about 2 inches. Color—near Dark Green, Plate 5G 3/4, but usually darker and being one or two shades darker than the foliage of all other so-called "Delicious" type apple varieties. Margin—coarsely serrate. Petiole—medium length (about 1 inch long); thick.

Flowers: Medium early (bloom about May 1st); large size. Color—white, with tinge of pink.

Fruit:

*Maturity when described.*—Hard ripe (date about October 1).

*Size.*—Uniform. Axial diameter—about 4 inches. Transverse diameter—about 3½ inches.

*Form.*—Conical-blocky.

*Cavity.*—Symmetrical. Depth—about ½ inch. Breadth—about 1¼ inches. Markings—none.

*Basin.*—Symmetrical; flaring; wide base.

*Stem.*—Stout; about 1 inch long.

*Calyx.*—Closed; broadly lanceloate; about ¼ inch long; reflexed from base at apex; both outer and inner surfaces pubescent.

*Eye.*—Small; partially closed.

*Skin.*—Thick; tough; smooth; waxed. Dots—obscure; few; small; even; color—from Pale Pink, Plate 8.5R 9/3 to Moderate Pink, Plate 10R 8/5; distribution—fairly even over most of skin, but somewhat more numerous toward calyx end of fruit. Ground color—near Dark Red, Plate 2.5R 3/7 but usually darker. Color markings—blushed; bright velvety red over all.

*Bloom.*—Wanting.

*Scarfskin.*—Wanting.

*General color effect.*—Deep full red.

*Flesh.*—Juicy. Color—satiny white. Texture—firm; crisp. Flavor—mild; rich. Aroma—distinct. Quality—best.

*Core.*—Median; Bundle area—medium size; cordate. Halves of core—unequal. Bundles—conspicious; in one whorl; color—green. Calyx tube—glabrous; broadly obconic; urn-shaped; depth of tube to shoulder—about ¼ inch; entire depth—about ½ inch. Styles—present; distinct; pubescent. Stamens—in one distinct whorl. Auxiliary cavity—present. Seed cells—open; cell walls—distinct; thick; length—about ½ inch; breadth—about 5/16 inch; longitudinal section—broadly oval; surface—fissured; cross section—broad.

Seeds:

*Number.*—Usually about 5 perfect and 4 imperfect average of usually 2 seeds per cell. Length—about ¼ inch. Breadth—about ⅛ inch.

*Form.*—Obtuse.

*Color.*—Dark brown.

Use: Market; dessert.

Keeping quality: Good.

Shipping quality: Good.

Disease and insect resistance: Comparable to that of other varieties such as "Jonathan," "Rome Beauty," "Staymen Winesap," Mood ("Starking Delicious"), etc., grown in the same or nearby orchards under the same cultural conditions; no disease or insect damage has been observed over several seasons, with crops given same care and same spraying program as other varieties referred to above.

I claim:

A new and distinct variety of apple tree, substantially as herein shown and described, characterized particularly as to novelty by the unique combination of a true semi-dwarf habit of growth, exceptionally large and lush Dark Green leaves which are one or two shades darker than the leaves of all other so-called "Delicious" type apple varieties; early, heavy and true spur-type fruit bearing habits, relatively large fruit size, early and uniform coloring habit of fruit throughout the tree irrespective of uniform exposure to sun and proximity of fruit, an attractive and distinct full Dark Red fruit color which is free of stripping and markings at maturity, an outstanding and true "Delicious" type fruit flavor, and good keeping and shipping qualities of the fruit.

No references cited.

UNITED STATES PATENT OFFICE

CERTIFICATE OF CORRECTION

Plant Patent No. 2,433 August 11, 1964

Gilbert Miller

It is hereby certified that error appears in the above numbered patent requiring correction and that the said Letters Patent should read as corrected below.

In the grant, line 3, and in the heading to the printed specification, lines 4 and 5, for "a corporation of Virginia", each occurrence, read -- a corporation of West Virginia --.

Signed and sealed this 19th day of January 1965.

(SEAL)
Attest:

ERNEST W. SWIDER
Attesting Officer

EDWARD J. BRENNER
Commissioner of Patents